United States Patent [19]

Greene

[11] Patent Number: 4,689,216

[45] Date of Patent: Aug. 25, 1987

[54] SANGUINARINE DENTAL COMPOSITIONS WITH HYDRATED SILICA

[75] Inventor: James A. Greene, Fort Collins, Colo.

[73] Assignee: Vipont Laboratories, Inc., Fort Collins, Colo.

[21] Appl. No.: 841,793

[22] Filed: Mar. 20, 1986

[51] Int. Cl.[4] .......................... A61K 7/16; A61K 7/26
[52] U.S. Cl. .......................................... 424/58; 424/49
[58] Field of Search ................................... 424/49, 58

[56] References Cited

U.S. PATENT DOCUMENTS

| | | | |
|---|---|---|---|
| 4,145,412 | 5/1979 | Ladanyi | 424/58 |
| 4,272,513 | 6/1981 | Gaffar | 424/58 |
| 4,325,939 | 4/1982 | Shah | 424/52 |
| 4,335,110 | 6/1982 | Collins | 424/58 |
| 4,559,224 | 12/1985 | Raaf | 424/49 |

OTHER PUBLICATIONS

Thorne et al., *J. Soc. Cosmet. Chem.*, 37, 279–286 (1986).
Chemberlain et al., 62nd *General Session International Association for Dental Research*, American Association for Dental Research, Dallas, Tex., Mar. 15–18, 1984.
American Dental Association, *Journal of Dental Research*, 55 (4), 563 (1976).

*Primary Examiner*—Johnnie R. Brown
*Assistant Examiner*—F. T. Moezie
*Attorney, Agent, or Firm*—Eric P. Schellin

[57] ABSTRACT

Dentifrices containing sanguinarine of superior stability and increased uptake into dental plaque are attained by the inclusion of hydrated silica as an abrasive.

6 Claims, No Drawings

SANGUINARINE DENTAL COMPOSITIONS WITH HYDRATED SILICA

FIELD OF THE INVENTION

This invention relates to novel sanguinarine containing dentifrices having hydrated silica in amounts sufficient to provide enhanced uptake of sanguinarine into dental plaque.

BACKGROUND OF THE INVENTION

*Sanguinaria canadensis* is known as Bloodroot, Puccoon, Tetterwort, etc and is an herb native to North America. The plant and its juices have been used for various purposes during pre-history as well as written history. It has been used as a natural historic folk remedy medicine. The plant has been generally used whole, either undried (fresh) or dried. The usual procedure is to powder the dried plant and mix it with a carrier. This folk remedy has been tried for such things as asthma, bronchitis, dysentery, ringworm, and a substantial list of other ailments.

Sanguinarine, chelerythrine and other benzophenanthridine alkaloids are known materials in Bloodroot and recovery of these materials involve procedures which include one or more chromatographic separation steps. However, this is not feasible for commercial purposes of producing an innocuous extract from the rhizome of bloodroot.

The use of an extract of Sanguinaria canadensis as an ingredient in oral cleansing preparations, in particular, toothpaste, is disclosed in U.S. Pat. No. 4,145,412.

This extract is produced by treating a finely cut or ground bloodroot with an organic solvent, such as methanol. The bloodroot is thoroughly stirred with several volumes of the solvent, and is maintained in the solvent for 24 hours or more, at a temperature of about 60° C. Subsequently, the solution is filtered and the methanol is evaporated. The residue is dissolved in chloroform, treated with concentrated hydrochloric acid, filtered and then dried. This dried extract is generally taken up in warm glycerine (65° C.) for mixing with a carrier.

The extract, when combined with a dentifrice or oral care product is an excellent breath freshener, and also an anti-plaque and anti-gingivitis agent; however, it is bount or sorbed by abrasives such as dicalcium phosphate and is shifted to the pseudo base form at pH's greater than 6.0. The normal pH's of dicalcium phosphate containing dentifrices is alkaline. Zinc chloride may be added to di-calcium phosphates to lower the pH. Zinc chloride has also been used in dentifrices for their anti-plaque properties; however, zinc chloride imparts an acrid mouth taste. Typical zinc compounds and derivatives used in dental compositions are set forth in U.S. Pat. No. 4,325,939.

It is therefore highly desirable to provide a dentifrice containing an extract of Sanguinarine Canadensis L. of improved stability, with increased uptake in dental plaque of sanguinarine chloride, without the use of a di-calcium phosphate or other alkaline abrasives, and zinc chloride.

SUMMARY OF THE INVENTION

In accordance with the invention, novel dentifrices containing sanguinarine chloride of superior stability and increased uptake into dental plaque are attained by the inclusion of hydrated silica as an abrasive.

DETAILED DESCRIPTION OF THE INVENTION

A dentifrice possessing a low level of abrasion for cleaning and polishing without damaging the hard tooth tissue (enamel, dentin, and cementum) and the chemotherepeutic anti-plaque and anti-gingivitis agent sanguinarine chloride will be desirable to remove undesirable dental deposits and prevent and/or retard their return; however, the addition of hydrated silica, provides a more stable sanguinarine chloride and increased uptake of sanguinarine chloride into dental plaque.

The desired dentifrice product should have an RDA (Radio Dentin Abrasivity) of less than 70, maintain a sanguinarine chloride level greater than 90% of input, and deliver an average plaque up-take greater than 10 ug sanguinarine chloride per gram of wet plaque.

Abrasives such as dicalcium phosphate, well known for their abrasive properties, have been used to formulate sanguinarine chloride containing dentifrices. A typical sanguinarine dentifrice containing dicalcium phosphate may have an RDA [Radiactive Dentin Abrasion as determined by the American Dental Association (*Journal of Dental Research,* 55 (4) 563, 1976)] of 60 and a typical plaque up-take of 3.9 ug±1.9 ug. However calcium interfers with sanguinarine chloride uptake into plaque, in vitro.

On the other hand, it is unexpectantly found that hydrated silica allows increased sanguinarine uptake and improves the sanguinarine stability in dentifrice formulations.

Hydrated silica is a jelly-like precipitate obtained when sodium silicate solution is acidified. The formula is $SiO_2 \cdot nH_2O$. The proportion of water in hydrated silica varies with the conditions of preparation and decreases gradually during drying. During drying, the jelly is converted to white amorphous power or lumps.

To make toothpaste, the hydrated silica is dispersed in a dental vehicle which preferably contains a liquid which is water and/or a humectant such as glycerine, sorbitol, xylitol, propylene glycol or polyethylene glycol 400 (including suitable mixture thereof). The preferred amount of hydrated silica is about 2% by weight of the dentifrice, however, the effective uper limit for the hydrated silica can be as high as 99.97% by weight when the dentfrice is a tooth-powder.

It is advantageous to use both water and a humectant when making the toothpaste. The total liquid content is generally over 20% by weight of the vehicle (sorbitol, which is present in admixture with water is considered a liquid for this purpose). The preferred humectants are glycerine and sorbitol. Typically the vehicle contains 0–80% by weight of glycerine, up to about 80% by weight of sorbitol and about 5–80% of water.

The sanguinarine, being water-soluble, is dissolved in an aqueous solution acidified with citric acid to a pH of approximately 2.5. The aqueous solution is added directly to the formulation.

The vehicle may also contain a thickening or gelling agent, such as natural and synthetic gums and gum-like materials, such as Irish Moss, gum tragacanth, alkali metal (e.g. Li, K, Na) carboxymethyl cellulose and hydroxymethyl carboxyethyl cellulose, polyvinyl pyrrolidone, starch, xylitol, water soluble hydrophillic collodial carboxyvinyl polymers such as those sold under the trademark Carbopol 934 and 940, hydroxyethyl cellulose, India gum, locust bean gum, agar agar, acacia gum, and Laponite CP or SP, which are synthetic inorganic complex silicate clays sold under trademark by Laporte Industries, Ltd. and pectin or inorganic thickners such as collodial silica, e.g. synthetic finely divided silica including those sold under the trademarks Cab-O-Sil M5, Syloid 244, Syloid 266, Syloid 2, Syloid 15, and Aerosil D200. The solid portion of the vehicle is typically present in an amount up to about 10% by weight of the toothpaste and preferably within the range of about 0.5–8% by weight. Inorganic silica is the thickener of choice.

The toothpaste can also contain surface-active agents, e.g. to achieve increased prophylactic action, assist achieving thorough and complete dispersion of the composition throughout the oral cavity and to render the composition cosmetically acceptable. The organic surface active material may be anionic, non-ionic, ampholytic, or cationic in nature, and it is preferable that the surface-active agent be detersive and impart foam. Suitable types of such surfactants are water soluble salts of higher fatty acid monoglyceride monosulfates, such as sodium salts of the monosulfated monoglycerides, or hydrogenated coconut oil fatty acids, higher alkyl sulfate, such as sodium lauryl sulfate, alkyl aryl sulfonates, such as sodium dodecyl benzene sulfonate, higher alkyl sulfoacetates, higher fatty acid esters of 1, 2-hydroxy propane sulfonates and the substantially saturated higher alphatic amino carboxylic acid compounds, such as those having 12 to 16 carbons in the fatty acid alkyl or acyl radicals, and the like. Examples of the last mentioned amides are N-lauroyl sarcosine, and sodium and potassium and ethanolamine salts of N-lauryl, N-myristyl or N-palmital sarcosinate, which should be free from soap.

Other suitable surfactants include non-ionic agents such as condensates of sorbiton monostearate with approximately 60 moles of ethylene oxide with propylene condensates of propylene oxide (Pluronics), and cationic surface active germicides and antibacterial compounds such as di-isobutylphenoxyethyldimethyl benzyl ammonium chloride, tertiary amines having one fatty alkyl group (from 12 to 18 carbon atoms) and (poly)ethylene groups attached to the nitrogen (typically containing a total of from about 2 to 50 ethanoxy groups per molecule) and salts thereof with acid and compounds of the structure

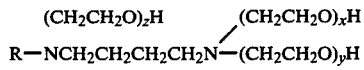

where R is a fatty alkyl group containing from about 12 to 18 carbon atoms, and x, y, z total 3 or higher, as well as salts thereof with mineral organic acids may also be used. It is preferred that the total amount of surfactant be from about 0.05–to about 5.0% by weight.

Other materials which may be incorporated in the dentifrice preparations of this invention include i.e. coloring agents or whitening agents such as titanium dioxide, preservatives, silicone, and chlorophyll compounds, each being incorporated in the instant toothpaste at about 5%.

The toothpaste also contains zinc compounds having a beneficial effect on oral mal-odor and product pH, such as those set forth in U.S. Pat. No. 4,325,939, to include zinc chloride, and zinc ammonium citrate.

The composition of the present invention may also contain a fluroine containing compound for protection of the teeth against decay. Examples include sodium monofluorophosphate, sodium fluoride, stannous fluoride ($SnF_2KF$) and amine fluorides.

The dentifrice may be prepared by suitably mixing the ingredient. For instance, a gelling agent such as carboxy methyl cellulose and a peservative such as sodium benzoate are dispersed with a humectant and water. A dental abrasive agent, surfactant, and flavor are then added. The resulting paste is then deareated (e.g. in vacuo) and tubed.

The examples given will illustrate the invention in further, but non-limiting detail, as follows:

EXAMPLE 1

A toothpaste is prepared according to the following formulation in order to determine stability and plaque uptake.

| Opaque Fluoride Gel Toothpaste - Rootbeer/Wintergreen Flavor | | |
|---|---|---|
| RAW MATERIAL | % w/w | GRAMS FOR 4000 g TOTAL |
| Carboxy methyl Cellulose | 1.60 | 64.00 |
| Sorbitol, USP 70% | 20.50 | 820.00 |
| DEIONIZED WATER | 29.90 | 1196.00 |
| $TiO_2$ USP | 4.00 | 160.00 |
| NaMFP Ozark Mahoning | .80 | 32.00 |
| Sodium Saccharine, Sherwin Williams | .20 | 8.00 |
| Fluid Extract JAW-002-108 (Sanguinarine Chloride) | 7.50 | 300.00 |
| Hydrated silica, SYLOX 15 WR Grace | 12.00 | 480.00 |
| Hydrated silica, HSG 753 WR Grace | 11.00 | 440.00 |
| Flavor 13560766 IFF | 1.00 | 40.00 |
| Sodium Lauryl Sulfate | 1.50 | 60.00 |
| Sorbitol, USP 70% | 10.00 | 400.00 |
| | 100.00 | 4000.00 |

4000 Grams were made on day 1
 2 Tubes for *SaCl, pH measurement 20 Tubes at 40° C.
 4 tubes centrifuged for viscosity measurements remainder in mixer for tubing
*Sanguinarine chloride
SaCl 271.8 ug/g
 31 tubes on day 3
 1 for plaque uptake on day 5–6 tubes of 300 grams were taken for RDA test. On day 5 RDA=92

| STABILITY Opaque Fluoride Gel Toothpaste - Rootbeer/Wintergreen Flavor | | | | | | | |
|---|---|---|---|---|---|---|---|
| | INITIAL | DAY 3 | DAY 5 | DAY 6 | DAY 7 | Day 14 | 4 WEEK |
| AMBIENT | | | | | | | |
| S-ug/g | 274.7 | 258.0 | 269.9 | | 274.5 | 268.5 | 258.1 |
| F-ug/g | | 940 total | 976 total | 176.0 available | | | |
| pH | | | | | | | 6.20 |

STABILITY
Opaque Fluoride Gel Toothpaste - Rootbeer/Wintergreen Flavor

|  | INITIAL | DAY 3 | DAY 5 | DAY 6 | DAY 7 | Day 14 | 4 WEEK |
|---|---|---|---|---|---|---|---|
| 40° C. |  |  |  |  |  |  |  |
| S-ug/g |  | 252.0 | 266.0 |  | 273.5 | 258 | 236.6 |
| F-ug/g |  | 2038 total | 172.5 available |  |  |  |  |
| pH |  |  |  |  |  |  | 6.29 |

RDA is 90. The plaque uptake is 12±5.2

EXAMPLE 2

A tooth paste is prepared according to the following formulation:

| PART | RAW MATERIAL | SUPPLIER | % w/w |
|---|---|---|---|
| A | Carboxy methyl Cellulose CMC 12M31P | HERCULES | 1.60 |
|  | SORBITOL USP, 70% | ICI | 27.90 |
| B | DEIONIZED WATER | Vipont | 24.45 |
|  | TiO$_2$ USP | WETTAKER, CLEARK & DANIELS | 4.00 |
|  | NaMFP | OZARK MAHONING | .80 |
|  | SODIUM SACCHARIN | SHERWIN WILLIAMS | .20 |
|  | ZnCl$_2$ USP |  | .05 |
| C | VIPONT FLUID EXTRACT (Sanguinarine Chloride) | Vipont | 7.50 |
|  | Hydrated silica SYLOX 15 | W.R. Grace | 12.00 |
| D | Hydrated silica SILICA HSG 753 | W.R. Grace | 9.00 |
| E | SODIUM LAURYL SULFATE | Albright & Wilson | 1.50 |
|  | SORBITOL USP, 70% | ICI | 10.00 |
| F | IFF FLAVOR 13560776 | IFF | 1.00 |
|  |  |  | 100.00 |

Initial batch not versated—in glass jar—pH 6.25
Versated—day 2—pH 6.28
96 Tubes Arrived on Day 2
 Initial 3
 3 for Tube Weight
 6 @40° C. Vipont
 51 @40° C. CSU
 33 @RT Vipont
Tube Weights: Day 2
 1. 77.61 g
 2. 77.78 g
 3. 77.84 g
Viscosity: Used Brookfield RVTD
 T-E Spindle
 5 RPM for 60 Sec 21° C.
Reading (XX.X)×(10,000) multiplication factor centipois
Day 2=48 hrs after completion 4.83×10$^5$ Centipois @60 Sec.
Day 6
 6.07×10$^5$ Centipois @60 Sec.
Day 20
 7.01×10$^5$ Centipois @60 Sec.
Specific Gravity: Day 15 1.4049 g/ml. Plaque uptake of 10.4±4.

STABILITY

|  | INITIAL | Day 1 Vipont Initial | DAY 2 | DAY 4 | DAY 8 | DAY 15 | DAY 22 |
|---|---|---|---|---|---|---|---|
|  |  |  | STABILITY |  |  |  |  |
| RT |  | (Jar 219.75) |  |  |  |  |  |
| S-ug/g |  | 233.79 | 212.60 | 206.75 | 182.28 | 212.07 | 214.57 |
| Total |  | 940 | 1000 |  | 1158 |  |  |
| F-ug/g |  |  |  |  |  |  |  |
| Ionic |  |  | 95 |  | 68 |  |  |
| F-ppm |  |  |  |  |  |  |  |
| pH |  | 6.25 | 6.28 |  |  |  |  |
| 40° C. |  |  |  |  |  |  |  |
| S-ug/g |  |  |  | 216.87 | 207.27 | 202.43 | 193.14 |
| Total |  |  |  | 1025 | 1084 | 1046 | 1042 |
| F-ug/g |  |  |  |  |  |  |  |
| Ionic |  |  |  | 72 | 75 | 69 | 49 |
| pH |  |  |  |  |  |  |  |

Day 1 Jar Before Versation 233.79 SaCl
Day 2 Jar After Versation 219.75 SaCl
Day 15 Marbeling observed in past—A separation Phenomena

EXAMPLE 3

A toothpaste is prepared according to the following formulation:

| PART | RAW MATERIAL | % w/w | Grams for 2000 g Total |
|---|---|---|---|
| A | CMC 12M31P HERCULES | .40 | 8.00 |
|   | SORBITOL USP, 70% | 52.00 | 1040.00 |
|   | DEIONIZED WATER | 3.60 | 72.00 |
| B | NaMFP OZARK MAHONING | .80 | 16.00 |
|   | SODIUM SACCHARIN SHERWIN WILLIAMS | .20 | 4.00 |
|   | ZnCl₂ USP | | .05 |
|   | Vipont | 7.50 | 150.00 |
| C | FLUID EXTRACT JWM-002-136 (Sanguinarine Chloride) Hydrated Silica | 12.00 | 240.00 |
| D | SYLOX 15 W.R. Grace Hydrated Silica | 11.00 | 220.00 |
|   | HSG 753 W.R. Grace | | |
| E | FLAVOR 13560776 | 1.00 | 20.00 |
| F | SODIUM LAURYL SULFATE | 1.50 | 30.00 |
|   | SORBITOL USP, 70% | 10.00 | 200.00 |
|   | | 100.00 | 2000.00 |

2000 Grams made on Day 1    10 Tubes Centrifuged 4 @ 40° C.
2 Tubes with Red 40
8 Tubes Uncentrifuged
1% Solution Red 40 16 Drops added to Approx. 200 g
16 drops Solution + .66 g
Formulate .33% 8% Red 40 solution in Colored Gel Centrifuged Called JMW-003-004a
for pilot purposes
used .35% for pilot application
on Day 5 = 290.48 SaCl

| PART | RAW MATERIAL | % w/w | Grams for 1000 g Total |
|---|---|---|---|
| G | Sodium Lauryl Sulfate | 2.00 | 20.00 |
|   | Flavor WL, 17976 | 1.00 | 10.00 |
| H | Vipont Fluid Extract (Sanguinarine Chloride) JRW-001-097 | 7.50 | 75.00 |
|   | Deionized Water | 3.80 | 38.00 |
|   | | 100.00 | 1000.00 |

An attempt was made to add silica in order to stop separation observed in the toothpaste, however; while more silica causes a thicker mixture, it is not determinal.
1000 Gram Batch Prepared was prepared on Day 1
2 tubes of Centrifuged, 1 in 40° oven
2 Tubes not Centrifuged in 40° Oven
1 Tube for Analysis of SaCl on Day 2
More silica causes thicker mixture, but not detrimentally so
On day 5 the SaCl=210.25 ug/g
The plaque up take is 5.3±1.8

EXAMPLE 5

VIADENT TOOTHPASTE with 40% Dical+2% Silica

Preparation of Viadent with Silica to Stop the Separation problems in Dical Toothpaste

STABILITY

|  | INITIAL | DAY 1 | DAY 2 | DAY 4 | DAY 14 | DAY 21 | 1 MONTH | 2 MONTH | 3 MONTH |
|---|---|---|---|---|---|---|---|---|---|
| RT |  |  |  |  |  |  |  |  |  |
| S |  | 204.5 | 215.4 | 207.32 | 218.25 | 208.30 | 206.85 | 215.78 | 208.08 |
| Total F ug/g |  | 1080 |  |  |  |  | 954 | 1016 | 974 |
| Ionic F ppm |  | 68 | 113 |  |  |  | 59 | 46.5 | 61 |
| pH |  |  |  | 6.27 |  |  | 6.32 |  |  |
| 40° C. |  |  |  |  |  |  |  |  |  |
| S |  |  |  | 205.76 | 202.9 | 193.96 | 185.40 | 173.76 | 160.30 |
| Total F ug/g |  |  |  | 1002 | 898 | 1025 | 1449 | 1046.7 | 982 |
| Ionic F ppm |  |  |  | 96 | 68 | 76 | 65 | 46.8 | 59 |
| pH |  |  |  |  |  |  |  |  |  |
| RDA of 90 |  |  |  |  |  |  |  |  |  |

EXAMPLE 4

A toothpaste is prepared according to the following formulation with 2% hydrated silica for sanguinarine visual stability, as follows:

| PART | RAW MATERIAL | % w/w | Grams for 1000 g Total |
|---|---|---|---|
| A | Glycerin, USP 96% | 12.00 | 120.00 |
|   | Sorbitol, USP 70% | 12.00 | 120.00 |
| B | Carrageenan | 1.40 | 14.00 |
| C | Deionized Water | 4.00 | 40.00 |
|   | Sodium Saccharin, USP Sherwin Williams | .30 | 3.00 |
| D | Deionized Water | 7.00 | 70.00 |
|   | Zinc Chloride | 2.00 | 20.00 |
|   | Hydrated Silica | | |
| E | Dicalcium Phosphate Dihydrite | 42.00 | 420.00 |
|   | Silka H & G 753, WR Grace | 2.00 | 20.00 |
| F₁ | Titanium Dioxide, USP | 3.00 | 30.00 |

| PART | RAW MATERIAL | % w/w | Grams for 1000 g Total |
|---|---|---|---|
| A | Glycerin, USP 96% | 12.00 | 120.00 |
|   | Sorbitol, USP 70% | 12.00 | 120.00 |
| B | Carrageenan | 1.40 | 14.00 |
| C | Deionized Water | 4.00 | 40.00 |
|   | Sodium Saccharin, USP Sherwin Williams | .30 | 3.00 |
| D | Deionized Water | 7.00 | 70.00 |
|   | Zinc Chloride, Amway | 2.00 | 20.00 |
| E | Dicalcium Phosphate Dihydrite | 42.00 | 420.00 |
|   | Hydrated Silica H & G 753, WR Grace | 2.00 | 20.00 |
| F | Titanium Dioxide, USP | 3.00 | 30.00 |
| G | Sodium Lauryl Sulfate | 2.00 | 20.00 |
|   | Flavor WL, 17976 | 1.00 | 10.00 |
| H | Vipont Fluid Extract (Sanguinarine Chloride) JRW-001-097 | 7.50 | 75.00 |
|   | Deionized Water | 3.80 | 38.00 |
|   | | 100.00 | 1000.00 | a 1000 Gram Batch was made on day 1
2 Tubes Centrifuged, 1 @40° C.
2 Tubes as is @40° C.
Remainder in Beaker for bleeding observation. 2 tubes centrifuged and sent for SaCl Analysis on day 3.
On day 4 the SaCl=184.35 ug/g
RDA=56

| PART | RAW MATERIAL | % w/w | Grams for 2000 g Total |
|---|---|---|---|
| A | Carboxy methyl cellulose | 1.20 | 24.00 |
|   | SORBITOL USP, 70% ICI | 27.30 | 546.00 |
|   | DEIONIZED WATER | 24.45 | 489.99 |
| B | TiO$_2$ USP | 3.00 | 60.00 |
|   | NaMFP OZARK MAHONING | .80 | 16.00 |
|   | SODIUM SACCHARIN SHERWIN WILLIAMS | .20 | 4.00 |
|   | ZnCl$_2$ USP | .05 | 1.00 |
| C | VIPONT FLUID EXTRACT (Sanguinarine Chloride) JAW-003-016 | 7.50 | 150.00 |
| D | Hydrated silica | 8.00 | 160.00 |
|   | Hydrated silica | 15.00 | 300.00 |
| E | SODIUM LAURYL SULFATE Albright & Wilson | 1.50 | 30.00 |
|   | SORBITOL USP, 70% ICI | 10.00 | 200.00 |
| F | FLAVOR 13560776 IFF | 1.00 | 20.00 |
|   |   | 100.00 |   |

2000 grams made one day 1
8 Tubes of centrifuged in jar for Viscosity test and observation
10 tubes 7 CRT 3 @40° C.
300 ml beaker filled in lab for observation after 20 Days Showed some signs of separation in RT and 40° C. Samples. Consistency is much lighter and on the runny end of the need viscosity.
Day 1—Viscosity $3.01 \times 10^5$ centipois @60 Sec 23° C. Comparable to Example 3
Day 5—Viscosity $5.55 \times 10^5$ centipois @60 Sec. 20° C.
Day 7—SaCl=256.22 ug/g pH 6.14
Day 35—SACl=250.94 ug/g
Day 40—Total F—973 ug/g IONIC F=62.9 ug/g These hydrated silicas have proved most useful in improving the sanguinarine uptake in dental plaque in toothpaste, however, they may similarly be incorporated into toothpowders, dental creams, prophylaxis pastes, and denture pastes and creams.

The pH of the dentifrices will generally be within the range of 5 to 7, more preferably from about 5.5 to 6.5.

The RDA is determined by the standard Missouri Analytical Method and the sanguinarine in plaque is determined by the analytical procedures described by Boulware, R. J. et al, Analysis of Sanguinarine in Dentifrices and Oral Rinses. J. Dent Res. 63: Abs. #1412 (1984) and Thorne, E. M. et. al HPLC analysis of Sanguinarine in Oral Health Care Products. J. Soc. Cos. Chem (1985).

The silicas used in Example 1 are sold under the name HSG-753 and Sylox 15. Those in Example 5 under the name Zeosyl 200 and Zeodent 113.

It is understood that the foregoing detailed description is by way of illustration and that variations can be made within the invention scope without departing from the spirit of the invention:

What is claimed is:

1. A dentifrice having increased plaque uptake in sanguinarine chloride for enhanced gingivitis and periodontal control comprising: (a) sanguinarine chloride approximately 7.5% by weight and (b) a hydrated silica in amounts from about 2.0% to 99.97% by weight.

2. The dentifrices of claim 1, including dentifrice additives which produce the metal ions $Zn^{+2}$, $Sn^{+2}$, or $Sn^{+4}$.

3. The dentifrice of claim 2, containing a gelling agent and being free from the inclusion of dicalcium phosphate abrasives.

4. A dentifrice as in claim 3, including TiO$_2$ as an opacifier.

5. A dentifrice as in claim 3, including dentifrice additives which produce the metal ions $Zn^{+2}$, $Sn^{+2}$, or $Sn^{+4}$.

6. A dentifrice as in claim 4, including dentifrice additives which produce the metal ions $Zn^{+2}$, $Sn^{+2}$, or $Sn^{+4}$.

* * * * *